(12) United States Patent
Ignatyev et al.

(10) Patent No.: US 7,094,328 B2
(45) Date of Patent: Aug. 22, 2006

(54) STRONG ACIDS, PROCESS FOR THE PREPARATION THEREOF, AND USES THEREOF

(75) Inventors: Nikolai Ignatyev, Duisburg (DE); Michael Schmidt, Seeheim-Jugenheim (DE); Andreas Kühner, Darmstadt (DE); Volker Hilarius, Groß-Umstadt (DE); Udo Heider, Winchester (GB); Andriy Kucheryna, Duisburg (DE); Peter Sartori, Utting (DE); Helge Willner, Mühlheim/Ruhr (DE)

(73) Assignee: Merck Patent GmbH, Darmstadt (DE)

( * ) Notice: Subject to any disclaimer, the term of this patent is extended or adjusted under 35 U.S.C. 154(b) by 16 days.

(21) Appl. No.: 10/481,786

(22) PCT Filed: Jun. 11, 2002

(86) PCT No.: PCT/EP02/06360

§ 371 (c)(1),
(2), (4) Date: Dec. 23, 2003

(87) PCT Pub. No.: WO03/002579

PCT Pub. Date: Jan. 9, 2003

(65) Prior Publication Data

US 2004/0171879 A1    Sep. 2, 2004

(30) Foreign Application Priority Data

Jun. 27, 2001   (DE) ................. 101 30 940

(51) Int. Cl.
C25B 3/08    (2006.01)
(52) U.S. Cl. .............. 205/430; 429/199; 429/189; 429/324; 429/200; 429/203; 423/301; 423/323; 423/179.5; 568/16; 252/62.2; 562/808
(58) Field of Classification Search ......... 205/430; 429/199, 189, 324, 200, 203; 423/301, 323; 423/179.5; 568/16; 252/62.2; 562/808
See application file for complete search history.

(56) References Cited

U.S. PATENT DOCUMENTS

| 6,210,830 B1 * | 4/2001 | Sartori et al. ............. 429/199 |
| 6,264,818 B1 | 7/2001 | Heider et al. |
| 2002/0015884 A1 | 2/2002 | Schmidt et al. |
| 2002/0022182 A1 | 2/2002 | Heider et al. |

FOREIGN PATENT DOCUMENTS

| EP | 1162204 | 12/2001 |
| EP | 1178050 | 2/2002 |
| EP | 1205998 | 5/2002 |
| WO | WO 98/15562 | * 4/1998 |
| WO | WO 0021969 | 4/2000 |

OTHER PUBLICATIONS

Bishop et al., Partial Second-Order Effects in [AmBnX] System: Reinterpretation of the Fluorine-19 Nuclear Magnetic Resonance Spectrum of Cesium Trans-bis(trifluoromethyl)tetrafluorophosphate, J. Chem. Soc. (A), 1970, 1074-1076.*
Chan et al., Trifluoromethyl-substituted Fluorophosphates and Fluoroarsenates , Canadian Journal of Chemistry, 46, (1968) 1237-1248.*
Jander et al., Formation of trifluromethyllated fluoro phosphates by reaction of trimethyltrifluoromethyltin with phosphorus (v) fluoride, Justus Liebigs Annalen der Chemie (1969), 726, 19-24 (ABSTRACT).*
Pavlenko et al., Reaction of Tris(perfluoroalkyl) phosphine Oxides and Tris(perfluoroalkyl) Difluorophosphoranes with Fluoride Ion, Zhurnal Obshchie Khimii, 1989, 59, 3, 528-534 (ABSTRACT).*
Kita, F. et al. "Electronic Structures, and Electrochemical Properties of LIPF6-N(CF3)N" Journal of Power Sources (2001), 97-98, 581-583, XP004254576.
Pavlenko N V et al.: "Reaction of Tris(Perfluoroalkyl) Phosphine Oxides and Tris(Perfluoroalkl)Difluorophosphoranes with Fluoride Ion" Journal of General Chemistry USSR, Consultants Bureau, New York, US, BD. 59, NR. 3,1. Mar. 1, 1989 Seiten 469-476, XP002053432.
Jander, Jochen et al. "Formation of Trifluromethyllated Fluoro Phosphates by Reaction of Trimethyltrifluoromethyltin with Phosphorus(v) Fluoride" Justus Liebigs Ann, Chem (1969), 726, 19-24, XP0011088644.

* cited by examiner

*Primary Examiner*—James O. Wilson
*Assistant Examiner*—Chukwuma Nwaonicha

(57) ABSTRACT

The present invention relates to acids of the general formula [I], $[R_yPF_{6-y}]^-H^+$ [I], where y=1, 2 or 3, and in which the ligands R may be identical or different and R is a perfluorinated $C_{1-8}$-alkyl or aryl group or R is a partially fluorinated $C_{1-8}$-alkyl or aryl group, in which some of the F or H may have been substituted by chlorine. The present invention furthermore relates to a process for the preparation of the acids according to the invention, to salts comprising a cation and the anion of the acid according to the invention, and to a process for the preparation of the salts. The invention furthermore relates to the use of the acids and salts according to the invention.

21 Claims, No Drawings

STRONG ACIDS, PROCESS FOR THE PREPARATION THEREOF, AND USES THEREOF

The present invention relates to acids of the general formula [I]

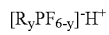   [I]

where
y=1, 2 or 3,
and in which
the ligands R may be identical or different, and
R is a perfluorinated $C_{1-8}$-alkyl or aryl group or R is a partially fluorinated $C_{1-8}$-alkyl or aryl group in which some of the F or H may have been substituted by chlorine.

The present invention furthermore relates to a process for the preparation of the acids according to the invention, to salts comprising a cation and the anion of one of the acids according to the invention, and to a process for the preparation of the salts. The invention furthermore relates to the use of the acids and metal salts according to the invention.

Hexafluorophosphoric acid, $HPF_6$, is used as a catalyst in organic chemistry or as a starting compound for the preparation of various salts. In the industry, hexafluorophosphoric acid is obtained by reaction [1] of phosphorus pentoxide and anhydrous hydrofluoric acid.

   [1]

Disadvantages of this process are the toxicity and the risk associated with handling the starting compound hydrogen fluoride, and the highly exothermic evolution of heat in the reaction.

Hexafluorophosphoric acid is commercially available as a 65% by weight aqueous solution. The solution is unstable at higher concentrations. Pure hexafluorophosphoric acid can be prepared in liquid sulfur dioxide, but is unstable at room temperature (D. E. C. Colbridge, Phosphorus. An Outline of chemistry, Biochemistry and Technology (Second Edition) Elsevier Scientific Publishing Comp. Amsterdam-Oxford-New York, 1980). The poor stability of highly concentrated hexafluorophosphoric acid solutions limits the potential uses of this acid as a catalyst. In addition, the coordination of the proton with the phosphorus hexafluoride anion reduces the proton activity of this acid.

The present invention therefore has the object of providing fluorophosphoric acid compounds which do not have the disadvantages of the prior art.

This object is achieved by an acid of the general formula [I]

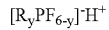   [I]

where
y=1, 2 or 3,
and in which
the ligands R may be identical or different, and
R is a perfluorinated $C_{1-8}$-alkyl or aryl group or R is a partially fluorinated $C_{1-8}$-alkyl or aryl group in which some of the F or H may have been substituted by chlorine.

The perfluorinated and the partially fluorinated alkyl or aryl groups R may be in the form of chain or ring structures.

Preference is given to acids in which at least one group R is a perfluorinated n-, iso-or tert-butyl group or a pentafluorophenyl group and is particularly preferably a pentafluoroethyl group.

Preference is furthermore given to acids in which y=2 or 3. Particular preference is given to acids in which y=3.

Particular preference is given to the acids according to the invention trifluorotris-(pentafluoroethyl)phosphoric acid, trifluorotris(nonafluoro-n-butyl)phosphoric acid, trifluorotris(heptafluoro-n-propyl)phosphoric acid, tetrafluorobis(nonafluoro-n-butyl)-phosphoric acid, pentafluoro(nonafluoro-n-butyl)phosphoric acid and tetrafluorobis-(heptafluoro-i-propyl)phosphoric acid.

For the nomenclature of fluorinated phosphoric acids, reference is made to the IUPAC nomenclature (A Guide to IUPAC Nomenclature of Organic Compounds. Recommendations, by R. Panico, W. H. Powell and Jean-Claude Richer, Blackwell Science, 1993).

The acids according to the invention have the advantage over the fluorophosphoric acids known hitherto of being easy to prepare, having high proton activity and being stable at room temperature in highly concentrated solution.

The present invention furthermore relates to a process for the preparation of the acids according to the invention in which a perfluoroalkylphosphorane is reacted with hydrogen fluoride in the presence of a suitable solvent and/or proton acceptor.

The preparation of perfluoroalkylphosphoranes as starting compounds for the process according to the invention is familiar to the person skilled in the art from the prior art, for example from German Patent Application DE 19 846 636 A1, which is incorporated herein by way of reference and is thus regarded as part of the disclosure.

Suitable solvents and/or proton acceptors for the processes according to the invention are preferably compounds having one, two or more of the following atoms: O, N, S, P, Se, Te and As.

Preference is given to water, alcohols, ethers, sulfides, amines, phosphines, carboxylic acids, esters, glycols, polyglycols, polyamines, polysulfides or mixtures of at least two of these solvents and/or proton acceptors.

Particularly preferred solvents and/or proton acceptors are water, methanol, ethanol, acetic acid, dimethyl ether, diethyl ether, dimethyl carbonate, dimethyl sulfide, dimethylformamide, triethylamine or triphenylphosphine, or mixtures of at least 2 of these compounds.

The concentration of hydrogen fluoride in the suitable solvent is preferably greater than 0.1% by weight of HF, particularly preferably greater than 5% by weight of HF and very particularly preferably greater than 10% by weight and most preferably greater than 20% by weight, but less than 100% by weight, of HF.

In a preferred embodiment, the reaction of the perfluoroalkylphosphorane in the processes according to the invention is carried out at a temperature of from −50 to +100° C., preferably at a temperature of from −35 to +50° C., particularly preferably at from 0 to 25° C.

By means of the process according to the invention, acids of the general formula [I] are readily accessible in high yields.

The present invention also relates to solutions of the acids according to the invention which have a concentration of greater than 2% by weight, preferably greater than 20% by weight, particularly preferably greater than 70% by weight, most preferably greater than 80% by weight, of the acid in a suitable solvent.

The solutions according to the invention, in particular in the high concentration ranges, enable proton activities which can only be achieved with difficulty with solutions of other fluorophosphoric acids. This is particularly advantageous on use of the acids according to the invention in highly concentrated form, for example as catalyst in a reaction mixture. A highly concentrated solution also avoids undesired dilution of reaction mixtures.

The present invention furthermore relates to salts of the general formula [II]

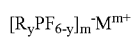

$$[R_yPF_{6-y}]_m^- M^{m+} \quad [II]$$

where
M$^{m+}$ is a monovalent, divalent or trivalent cation,
m=1, 2 or 3
and y=1, 2 or 3, and in which
the ligands R may be identical or different, and
R is a perfluorinated $C_{1-8}$-alkyl or aryl group or R is a partially fluorinated $C_{1-8}$-alkyl or aryl group in which some of the F or H may have been substituted by chlorine.

The cation M$^{m+}$ can be a metal cation or an organic cation.

Suitable organic cations are known to the person skilled in the art and are described, for example, in German Patent Application DE 10109032.3 on pages 4 to 6. This literature is incorporated herein by way of reference and is thus regarded as part of the disclosure.

The salts of the general formula [II] preferably contain an Li, Zn, Mg, Cu, Ag, ammonium, phosphonium, oxonioum, sulfonium, arsonium, tropilium, a a nitryl cation, a nitrosyl cation or a tris(dialkylammino)carbonium cation.

An advantage of the salts according to the invention is their good solubility in organic solvents.

In a preferred embodiment, these salts are prepared by a process in which an acid according to the invention is reacted in a suitable solvent with a salt of the general formula [III]

$$M^{m+}(A)^{m-} \quad [III]$$

where
M$^{m+}$ is a monovalent, divalent or trivalent cation,
A is a basic or neutral anion or a mixture of basic anions or a mixture of at least one basic and at least one neutral anion,
and m=1, 2 or 3, or with metals, metal hydrides, metal oxides or metal hydroxides.

The process is preferably carried out using salts of the formula [III] which contain at least one carbonate, chloride, fluoride, formate, acetate or trifluoroacetate anion.

The process is preferably carried out using anions which form readily volatile acids, such as, for example, hydrochloric acid, formic acid or acetic acid.

In the process, the metals employed are preferably Li, Na, K, Rb, Mg, Cs, Ca, Sr, Ba, Sc, Y, Yb, La, Al, In, Cd and/or Zn, the oxides employed are preferably $Li_2O$, $Na_2O$, $K_2O$, MgO, CaO, SrO, BaO, $Sc_2O_3$, $Y_2O_3$, $Yb_2O_3$, $La_2O_3$, $Al_2O_3$, CdO, ZnO, CuO, FeO and/or $Fe_2O_3$, the hydroxides employed are preferably LiOH, NaOH, KOH, RbOH, CsOH, $Mg(OH)_2$, $Ca(OH)_2$, $Sr(OH)_2$, $Ba(OH)_2$, $Cd(OH)_2$, $Zn(OH)_2$, $Sc(OH)_3$, $Al(OH)_3$ and/or $Cu(OH)_2$ and the hydrides employed are preferably LiH, NaH, $CaH_2$, $YH_3$ and/or $AlH_3$.

The process for the preparation of the salts according to the invention is simple to carry out and offers high yields.

In addition, the present invention relates to the use of one of the salts according to the invention as catalyst, as phase-transfer catalyst, as solvent, in particular as ionic liquid, or as conductive salt in the electrolytes of various electrochemical devices.

The person skilled in the art understands an "ionic liquid" to be organic compounds having an ionic structure and a low melting point, for example N,N-dialkylimidazolium salts [C. E. Song, E. J. Roh, Chem. Comm. (Camebridge) 2000, 10, pp. 837–838; J. Howarth, Tetrahedron Lett. 41 (2000) 34, pp. 6627–6629; C. E. Song, C. E. Oh, E. J. Roh, D. J. Choo, Chem. Comm. (Camebridge) 2000,18, pp.1743–1744).

The present invention also relates to the use of an acid according to the invention as catalyst in the preparation of organic compounds.

The acids according to the invention are particularly suitable as replacement for the acids $HPF_6$ and/or $HBF_4$ in chemical reactions.

The acids and/or salts according to the invention are preferably used in one of the following processes:
Processes for the
preparation of photosensitive polymers [CA (Chemical Abstracts) 110: 15956e],
preparation of dihydroxydiaryl compounds [CA 110: 94679t],
surface treatment of metals [CA 110: 139975e],
preparation of electrically conductive aniline polymers [CA 110: 155067r],
preparation of carboxylic acids and carboxylic acid esters [CA 110: 233613g],
preparation of high-molecular-weight diazonium compounds [CA 110: 87472n],
preparation of epoxy resins [CA 111: 135490r],
preparation of electrically conductive materials from amine-like compounds [CA 112: 46758n],
preparation of octadienols [CA 112: 98016p],
carboamination or carboamidation of olefins [CA 112: 161007d],
isomerisation of butenes [CA 112: 157653u],
preparation of electrically conductive polyalkoxythiophenes [CA 115: 50551u],
desulfuration of oil and effluent [CA 116: 261878q],
preparation of triglycidyltrimethylolalkane-based compositions [CA 117: 92344a],
preparation of polymers from styrene and carbon monoxide [CA 117: 172290v],
preparation of organic salts for the storage of information [CA 117: 17381g],
production of information carriers having good light resistance [CA 115: 267063w],
preparation of silicon support materials for catalysts [CA 117: 74989k], polymerisation of pyrrole derivatives [CA 117: 70577b],
copolymerisation of carbon monoxide and an olefinically unsaturated compound[CA 118: 7520h],
preparation of electrically conductive polymers [CA 118: 137707k],
preparation of magnetic contrast agents [CA 118: 299355x],
preparation of polymer coatings [CA 119: 54608y],
removal of oxide layers on stainless steel [CA 119: 77272y],
synthesis of methyl tert-butyl ether [CA 119: 202992m],
preparation of cyclic sulfonium salts containing 5–7 carbons [CA 119: 249826a],
preparation of cyclosiloxanes [120: 108008u],
refining of heavy oils and bitumen [CA 120: 195633k],
treatment of aluminium compounds [CA 120: 283104u],
preparation of quaternary pyridinium or anilinium salts [CA 121: 9165g],
copolymerisation of olefins and carbon monoxide [CA 121: 10209f],
preparation of aromatic hydroxylic compounds [CA 121: 133684q],
preparation of acetic ester derivatives [CA 121: 157308w],
preparation of resin from dialkenylbenzene and polyarylamines [CA 122: 70050c],
preparation of substituted pyrrolopyrimidin-4-ones [CA 122: 314562q],
recovery of petroleum [CA 122: 295102w],
use as non-aqueous battery electrolytes [CA 122: 118595j],
preparation of stable methyl cations [CA 124: 288639q],
preparation of cyclic sulfonium salts [CA 125: 114470h],
preparation of optical storage materials [CA 125: 127895a],
preparation of conjugated fluoropyridinium salts [CA 125: 119500c],
preparation of iridium/diphosphine complexes [CA 126: 226760e],
asymmetric hydrogenation of imines [CA 126: 225097g],
hydroformylation of unsaturated compounds [CA 126: 225032g],
synthesis of polymers [CA 126: 104554v],
preparation of polymers from polycycloolefins with silyl groups [CA 127: 110414m],
preparation of ruthenium catalysts [CA 127: 83071p],
preparation of ibuprofen [CA 127: 318741y],
preparation of cyclohexadienyl compounds [CA 126: 212225x],
copolymerisation of olefins [CA 126: 199931c],
preparation of inorganic methylimidazolinium salts [CA 128: 167423p],
preparation of SiCO and SiC ceramic fibres [CA 128: 234151p],
preparation of thermoprint materials [CA 128: 210892e],
preparation of polymers [CA 129: 317091r],
preparation of aziridine-polyether compounds [CA 131: 35901 v],
preparation of dicarboxylic acid diesters [CA 131: 199417t],
hydroxylation of aromatic hydrocarbons [CA 129: 218223d],
preparation of carboxylic acids and carboxylic acid esters [CA 129: 216347y],
pretreatment of lithographic printing plates [CA 129: 195815g].

The invention is explained below with reference to examples. These examples serve merely to explain the invention and do not restrict the general inventive idea.

The process according to the invention can be used to prepare, for example, trifluoro-tris(perfluoroalkyl)phosphoric acids in virtually quantitative yield by reaction of difluorotris(perfluoroalkyl)phosphoranes with hydrogen fluoride in suitable solvents. Surprisingly, this yield is virtually unimpaired by hydrolysis.

The process according to the invention can be used, for example, to prepare a highly concentrated aqueous solution of trifluorotris(pentafluoroethyl)phosphoric acid within a few minutes by reaction of difluorotris(pentafluoroethyl) phosphorane with 18.3% by weight aqueous HF. The reaction proceeds in accordance with the reaction equation [2]:

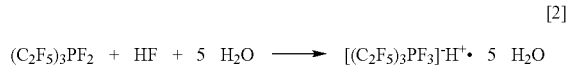

[2]

The resultant solution has a concentration of 83.2% by weight and is stable for a number of weeks at room temperature.

Acid concentrations of less than 83.2% by weight can also be prepared in this way, for example by dilution with a suitable solvent or by reaction of a phosphorane with more highly diluted hydrogen fluoride solution.

However, the reaction of phosphoranes with more-dilute aqueous hydrogen fluoride solutions, for example 2% by weight, take more time. In the case of more highly diluted aqueous hydrogen fluoride solutions, firstly an adduct of water and phosphorane is formed, and this is then slowly converted into the more stable product.

The rate of conversion of the adduct into the product is temperature-dependent. At room temperature, the conversion in accordance with reaction [2] in 2% by weight hydrogen fluoride solution takes 2 days. At –21° C. and under the same concentration ratios, only 30% of the adduct has converted into trifluorotris(pentafluoroethyl)phos-phoric acid within six days.

On reaction of the phosphorane in an ice bath in accordance with reaction equation [2] with a 4.3% by weight aqueous hydrogen fluoride solution, a mixture of phosphorane/water adduct and trifluorotris(pentafluoroethyl)phosphoric acid in the ratio 1:2 is formed within 2–3 minutes.

The reaction can be carried out at atmospheric pressure or superatmospheric pressure, if desired also under a protective-gas atmosphere.

Trifluorotris(pentafluoroethyl)phosphoric acid can exist in two different conformations, the meridional conformation and the facial conformation. The two structures exist in equilibrium. This equilibrium is dependent on the temperature and the hydrogen fluoride concentration in water during reaction of the starting materials. Initially, the meridional structure is formed, which then achieves an equilibrium with the facial structure.

The person skilled in the art understands that the proton in the strong acids according to the invention is in the form of a complex with the respective solvent. In the formulation of the formulae in the examples, the complex of proton and solvent has therefore not been formulated out.

The complete disclosure content of all applications, patents and publications mentioned above and below and of the corresponding application DE 101 30 940.6, filed on Jun. 27, 2001, is incorporated into this application by way of reference.

Even without further comments, it is assumed that a person skilled in the art will be able to utilise the above description in the broadest scope. The preferred embodiments and examples should therefore merely be regarded as descriptive disclosure which is absolutely not limiting in any way.

All NMR spectra were measured on a Bruker WP 80 SY spectrometer ($^1$H: 80 MHz, $^{19}$F: 75.47 MHz).

EXAMPLES

Example 1

3.74 g of water were added to 3.14 g of a 40% by weight aqueous hydrofluoric acid (62.8 mmol of HF) (in total 312.1 mmol of water) in an FEP (fluoroethylene polymer) flask. After this mixture had been cooled in an ice bath, 26.55 g (62.3 mmol) of difluorotris(pentafluoroethyl)phosphorane were added over the course of 2 minutes while stirring using a magnetic stirrer. All the phosphorane had dissolved within 3 minutes, and a colourless, clear solution of aqueous acid $[(C_2F_5)_3PF_3]^-H^+$ had formed. 33.4 g of an 83.2% by weight trifluorotris(pentafluoroethyl)phosphoric acid solution were prepared in virtually quantitative yield.

The compound conforms to the formula: $[(C_2F_5)_3PF_3]^-H^+ \cdot 5H_2O$.

The solution was analysed by $^{19}$F NMR spectroscopy. The spectra were measured using an FEP tube with an acetone-$D_6$ film as external lock and $CCl_3F$ as external reference.

$^{19}$F NMR, δ, ppm: −44.03 dm (PF); −80.61 m ($CF_3$); −82.47 m (2$CF_3$); −88.99 dm ($PF_2$); −115.36 dm (3$CF_2$); $J^1_{P,F}$=889 Hz; $J^1_{P,F}$=907 Hz; $J^2$P, F=92 Hz.

These signals belong to the meridional structure of the acid $[(C_2F_5)_3PF_3]^-H^+ \cdot 5H_2O$. Within 2 days, a new doublet formed in the $^{19}$F NMR spectrum at −67.41 ppm; $J^1_{P,F}$=786 Hz ($PF_3$ group), which can be assigned to the facial structure of the acid $[(C_2F_5)_3PF_3]^-H^+ 5H_2O$. No further changes were observed during storage at room temperature over the next 3 weeks. The 83.2% by weight acid formed an equilibrium mixture of about 90% of the meridional conformation and 10% of the facial conformation of the acid at room temperature.

Example 2

2.24 g of water were added to 1.88 g of a 40% by weight aqueous hydrofluoric acid solution (37.6 mmol of HF) (in total 186.8 mmol of water) in an FEP flask. 15.88 g (37.3 mmol) of difluorotris(pentafluoroethyl)phosphorane were added to the aqueous HF solution at room temperature over the course of 3 minutes while stirring the reaction mixture using a magnetic stirrer. Due to the exothermic reaction, temperatures of up to 50° C. were reached, while the phosphorane dissolved. 20.0 g of a colourless, clear solution of $[(C_2F_5)_3PF_3]^-H^+$ in water with a concentration of 83.2% by weight were formed in virtually quantitative yield.

The solution was analysed by $^{19}$F NMR spectroscopy. The spectra were measured using an FEP tube with an acetone-$D_6$ film as external lock and $CCl_3F$ as external reference.

$^{19}$F NMR (meridional conformation), δ, ppm: −44.46 dm (PF); −81.05 m ($CF_3$); −82.85 m (2$CF_3$); −89.54 dm ($PF_2$); −115.74 dm (3$CF_2$); $J^1_{P,F}$=889 Hz; $J^1_{P,F}$=905 Hz; $J^2_{P,F}$=93 Hz.

$^{19}$F NMR (facial conformation), δ, ppm: −67.82 dm ($PF_3$); $J^1_{P,F}$=784 Hz. Other signals of the facial conformation overlapped with the signals of the meridional conformation.

The spectra show that in this case both conformations of the acid, both the meridional and the facial conformation, are formed at the time of preparation of the solution.

Example 3

10.57 g of water were added to 3.91 g of a 40% by weight aqueous hydrofluoric acid solution (78.2 mmol of HF) (in total 716.8 mmol of water) in an FEP flask. After this mixture had been cooled in an ice bath, 33.34 g (78.2 mmol) of difluorotris(penta-fluoroethyl)phosphorane were added over the course of 3 minutes while stirring using a magnetic stirrer. All the phosphorane dissolved within this time, and a clear solution of $[(C_2F_5)_3PF_3]^-H^+$ was formed. 47.8 g of aqueous trifluorotris(pentafluoroethyl)-phosphoric acid (I) in a concentration of 73.0% by weight were obtained in quantitative yield.

hu 19F NMR ($CCl_3F$—external reference): −44.45 dm (PF); −80.84 m ($CF_3$); −82.57 m (2$CF_3$); −89.13 dm ($PF_2$); −115.75 dm (3$CF_2$); $J^1_{P,F}$=889 Hz; $J^1_{P,F}$=909 Hz; $J^2_{P,F}$=92 Hz.

The signals shown belong to the meridional structure of the acid $[(C_2F_5)_3PF_3]^-H^+$ and exhibited no changes in the spectrum within 5 days. The acid $[(C_2F_5)_3PF_3]^-H^+$ thus preferentially exhibits the meridional conformation in the present concentration at room temperature.

Example 4

12.46 g of water were added to 1.51 g of a 40% by weight aqueous hydrofluoric acid solution (30.2 mmol of HF) (in total 741.7 mmol of water) in an FEP flask. After this mixture had been cooled in an ice bath, 12.74 g (29.9 mmol) of difluorotris(penta-fluoroethyl)phosphorane were added over the course of 3 minutes while stirring using a magnetic stirrer. All the phosphorane dissolved in this period, and 26.7 g of a colourless, clear solution of the acid were obtained in virtually quantitative yield.

The $^{19}$F NMR spectrum showed the presence of two forms of hexacoordinated phosphorus. The first form is a complex of difluorotris(pentafluoroethyl)phosphorane with water:

$^{19}$F NMR ($CCl_3F$—external reference): −80.39 m ($CF_3$); −81.31m (2$CF_3$); −89.19 dm ($PF_2$); −113.78 dm (3$CF_2$); −164.59 s ($H_3O^+ \cdot HF$) $J^1_{P,F}$=846 Hz ; $J^2_{P,F}$=89 Hz.

The second form is the usual meridional conformation of trifluorotris(pentafluoro-ethyl)phosphoric acid $[(C_2F_5)_3PF_3]^-H^+$.

$^{19}$F NMR ($CCl_3F$—external reference): −44.60 dm (PF); −80.81 m ($CF_3$); −82.49 m (2$CF_3$); −89.34 dm ($PF_2$); −115.96 dm (3$CF_2$); $J^1_{P,F}$=889 Hz; $J^1_{P,F}$=884 Hz; $J^2_{P,F}$=95 Hz.

Within 4 days of storage at room temperature, the $^{19}$F NMR spectrum only showed the presence of the meridional conformation of trifluorotris(pentafluoroethyl)phosphoric acid $[(C_2F_5)_3PF_3]^{31}H^+$ in solution.

Example 5

29.60 g of water were added to 1.47 g of a 40% by weight aqueous hydrofluoric acid solution (29.4 mmol of HF) (in total 1691.6 mmol of water) in an FEP flask. After this mixture had been cooled in an ice bath, 12.47 g (29.3 mmol) of difluorotris(pentafluoroethyl)phosphorane were added over the course of three minutes while stirring using a magnetic stirrer. All the phosphorane dissolved within this period, and a colourless, clear solution of 43.5 g was prepared.

The $^{19}$F NMR spectrum showed that in this case principally the aqueous adduct is formed directly on addition of the phosphorane.

19F NMR (CCl$_3$F—external reference): −79.49 m (CF$_3$); −80.74 m (2CF$_3$); −88.60 dm (PF$_2$); −113.35 dm (3CF$_2$); −162.54 s (H$_3$O$^+$·HF) J$^1_{P,F}$=842 Hz; −J$^2_{P,F}$=89 Hz.

Within five days at room temperature, this adduct was converted completely into tris(pentafluoroethyl)trifluorophosphoric acid [(C$_2$F$_5$)$_3$PF$_3$]$^-$H$^+$. This was confirmed by $^{19}$F NMR spectroscopy.

Example 6

5.64 g (122.3 mmol) of dimethyl ether were cooled to −35° C. in an FEP flask using an ethanol bath. In succession, firstly 1.42 g (71.0 mmol) of hydrogen fluoride (HF) were slowly added to the reaction mixture and subsequently 30.25 g (71.0 mmol) of difluorotris(pentafluoroethyl)phosphorane were added over the course of five minutes while the reaction mixture was stirred using a magnetic stirrer. When the phosphorane had dissolved and the reaction mixture had warmed to room temperature, 37.3 g of a colourless, clear solution were obtained.

This solution was analysed by $^{19}$F NMR spectroscopy. The spectra were measured using an FEP tube with an acetonitrile-D$_3$ film as external lock and CCl$_3$F as internal reference.

The $^{19}$F NMR spectrum showed that in this case the acid [(C$_2$F$_5$)$_3$PF$_3$]$^-$H$^+$ is preferentially formed with the meridional structure.

$^{19}$F NMR of the meridional conformation: −43.58 dm (PF); −80.19 m (CF$_3$); −81.90 m (2CF$_3$); −87.03 dm (PF$_2$); −115.51 dm (3CF$_2$); J$^1$P,F=888 Hz; J$^1_{P,F}$=894 Hz; J$^2_{P,F}$=94 Hz.

Within three days, the concentration of the facial conformation of the acid [(C$_2$F$_5$)$_3$PF$_3$]$^-$H$^+$ in the mixture increased.

$^{19}$F NMR spectrum of the facial conformation: −66.12 dm; J$^1_{P,F}$=798 Hz (PF$_3$ group).

Other signals of the facial conformation overlapped with the signals of the meridional conformation.

No further changes in the $^{19}$F NMR spectra were observed within five weeks during storage at room temperature.

Example 7

6.04 g (81.5 mmol) of dry diethyl ether in an FEP flask were cooled by means of an ice bath. While stirring using a magnetic stirrer, firstly 0.92 g (45.9 mmol) of hydrogen fluoride (HF) was slowly added to the diethyl ether and then 18.67 g (43.8 mmol) of difluorotris(pentafluoroethyl)phosphorane were added over the course of 5 minutes. After dissolution of the phosphorane within one to two minutes and warming of the reaction mixture to room temperature, 25.6 g of a colourless, clear solution were formed.

This solution was analysed by $^{19}$F NMR spectroscopy. The spectra were measured using an FEP tube with an acetonitrile-D$_3$ film as external lock and CCl$_3$F as internal reference.

The $^{19}$F NMR spectrum showed that the acid [(C$_2$F$_5$)$_3$PF$_3$]$^-$H$^+$ is formed in two conformations.

$^{19}$F NMR of the meridional conformation (approximately 85 mol %): −43.68 dm (PF); −80.00 m (CF$_3$); −81.71 m (2CF$_3$); −86.93 dm (PF$_2$); −115.31 dm (3CF$_2$); J$^1_{P,F}$=890 Hz; J$^{P,F}$=897 Hz; J$^2_{P,F}$=92 Hz.

$^{19}$F NMR spectrum of the facial form (approximately 15 mol %): −67.37 dm; J$^1_{P,F}$=793 Hz (PF$_3$ group). Other signals of the facial conformation overlapped with the signals of the meridional conformation.

No changes in the $^{19}$F NMR spectrum were observed within two months on storage at room temperature.

Example 8

3.33 g (103.9 mmol) of methanol in an FEP flask were cooled using an ice bath. While stirring using a magnetic stirrer, firstly 0.91 g (45.5 mmol) of hydrogen fluoride (HF) was slowly added to the methanol and 18.05 g (42.4 mmol) of difluorotris(pentafluoroethyl)phosphorane were added to the reaction mixture over the course of a further five minutes. After dissolution of the phosphorane and warming of the reaction mixture to room temperature, 22.2 g of a colourless, clear solution were obtained.

This solution was analysed by $^{19}$F NMR spectroscopy. The spectra were measured using an FEP tube with an acetonitrile-D$_3$ film as external lock and CCl$_3$F as internal reference.

The $^{19}$F NMR shows that in this case the acid [(C$_2$F$_5$)$_3$PF$_3$]$^-$H$^+$ is formed in two conformations.

$^{19}$F NMR of the meridional conformation (approximately 85 mol %): −43.80 dm (PF); −80.50 m (CF$_3$); −81.93 m (2CF$_3$); −87.50 dm (PF$_2$); −114.93 dm (3CF$_2$); J$^1_{P,F}$=887 Hz; J$^2_{P,F}$=95 Hz.

$^{19}$F NMR spectrum of the facial conformation (approximately 15 mol %): −66.44 dm; J$^1_{P,F}$=780 Hz. (PF$_3$ group). Other signals of the facial form overlapped with the signals of the meridional form.

No changes in the $^{19}$F NMR spectrum were observed within one month on storage at room temperature.

Example 9

3.02 g (48.8 mmol) of dimethyl sulfide (CH$_3$)$_2$S in an FEP flask were cooled by means of an ice bath. While stirring using a magnetic stirrer, firstly 0.98 g (49.0 mmol) of hydrogen fluoride (HF) and subsequently, over the course of five minutes, 20.88 g (49.0 mmol) of difluorotris(pentafluoroethyl)phosphorane were added to the dimethyl sulfide. When all the phosphorane had been added, the reaction mixture hardened completely. After additional mechanical stirring and drying of the reaction mixture at room temperature in a stream of argon protective gas, 23.9 g of a colourless, solid material were obtained.

0.4 g of this material was dissolved in acetonitrile-D$_3$, and this solution was analysed by $^{19}$F NMR spectroscopy. CCl$_3$F was used as internal reference.

The $^{19}$F NMR spectrum showed that in this case the acid [(C$_2$F$_5$)$_3$PF$_3$]$^-$H$^+$ is formed in the meridional conformation.

$^{19}$F NMR: 43.54 dm (PF); −79.66 m (CF$_3$); −81.25 m (2CF$_3$); −86.83 dm (PF$_2$); −115.28 dm (3CF$_2$); J$^1_{P,F}$=889 Hz; J$^1$, F=906 Hz; J$^2_{P,F}$=92 Hz.

Example 10

3.23 g (12.3 mmol) of triphenylphosphine (Ph$_3$P) in an FEP flask were cooled to −25° C. in an ethanol/dry ice bath. While the reaction mixture was stirred using a magnetic stirrer, firstly 0.66 g (33.0 mmol) of hydrogen fluoride (HF) was slowly added to the triphenylphosphine and then 5.25 g (12.3 mmol) of difluorotris(pentafluoroethyl)-phosphorane were added over the course of a further five minutes. When all the phosphorane had been added, the reaction mixture hardened completely. After additional mechanical mixing and drying of the reaction mixture at room temperature under a stream of argon protective gas, 8.8 g of a pale-yellow solid were obtained. 0.4 g of this material was dissolved in acetonitrile-$D_3$, and this solution was analysed by $^{19}F$ NMR spectroscopy. $CCl_3F$ was used as internal reference.

The $^{19}F$ NMR spectrum showed that in this case the acid $[(C_2F_5)_3PF_3]^-H^+$ as a complexes with triphenylphosphine is formed in the meridional conformation.

$^{19}F$ NMR: −43.65 dm (PF); −79.75 m ($CF_3$); −81.34 m ($2CF_3$); −86.99 dm ($PF_2$); −115.45 dm ($3CF_2$); $J^1P$, F=889 Hz; $J^1_{P,F}$=906 Hz; $J^2_{P,F}$=92 Hz.

A small signal of residual HF is visible in the $^{19}F$ NMR spectrum (−181.75 ppm). $^1H$ NMR: 7.8 m ($Ph_3PH^+$)

Example 11

1.71 g (23.4 mmol) of dimethylformamide, $HC(O)N(CH_3)_2$, in an FEP flask were cooled to −25° C. using an ethanol/dry ice bath. While stirring using a magnetic stirrer, firstly 0.566 g (28.3 mmol) of hydrogen fluoride (HF) was slowly added to the dimethylformamide and then 9.92 g (23.3 mmol) of difluorotris(pentafluoroethyl)-phosphorane were added at 0° C. over the course of five minutes. When all the phosphorane had been added, the reaction mixture was warmed to room temperature. 12.2 g of a high-density, virtually solid, white material were produced.

Small amounts of this material were dissolved in dimethylformamide and in acetonitrile-$D_3$, and these solutions were analysed by $^{19}F$ and $^1H$ NMR spectroscopy. $CCl_3F$ and TMS were used as internal reference.

The $^{19}F$ NMR spectrum showed that in this case the acid $[(C_2F_5)_3PF_3]^-H^+$ is formed in the meridional conformation.

$^{19}F$ NMR (solvent: acetonitrile-$D_3$): −43.64 dm (PF); −79.76 m ($CF_3$); −81.35 m ($2CF_3$); −87.08 dm ($PF_2$); −115.35 dm ($3CF_2$); $J^1_{P,F}$=889 Hz; $J^1_{P,F}$=906 Hz; $J^2_{P,F}$=90 Hz.

A small signal of residual hydrogen fluoride was again observed in the $^{19}F$ NMR spectrum (−182.30 ppm).

$^1H$ NMR (solvent: acetonitrile-$D_3$): 3.12 s ($CH_3$); 3.27 s ($CH_3$); 8.19 s (CH); 10.97 s ($H^+$).

$^{19}F$ NMR (solvent: dimethylformamide): −43.88 dm (PF); −79.76 m (CF3); −81.35 m ($2CF_3$); −87.08 dm ($PF_2$); −115.35 dm ($3CF_2$); $J^1_{P,F}$=889 Hz $J^1_{P,F}$=906 Hz; $J^2_{P,F}$=90 Hz.

A small signal of residual hydrogen fluoride was again observed in the $^{19}F$ NMR spectrum (−182.30 ppm).

Example 12

4.92 g (81.9 mmol) of acetic acid, $CH_3COOH$, in an FEP flask were cooled by means of an ice bath. While stirring using a magnetic stirrer, firstly 0.424 g (21.2 mmol) of hydrogen fluoride (HF) was slowly added to the acetic acid and then 8.83 g (20.7 mmol) of difluorotris(pentafluoroethyl)phosphorane were added over the course of five minutes. After the phosphorane had dissolved and the reaction mixture had been warmed to room temperature, 14.17 g of a colourless, clear solution were obtained.

This solution was analysed by $^{19}F$ NMR spectroscopy. The spectra were measured using an FEP tube with an acetone-$D_6$ film as external lock and $CCl_3F$ as external reference. In this example, the $^{19}F$ NMR spectrum shows that the acid $[(C_2F_5)_3PF_3]^-H^+$ is preferentially formed in the meridional structure.

$^{19}F$ NMR of the meridional form: −44.65 dm (PF); −80.94 m ($CF_3$); −82.58 m ($2CF_3$); −88.59 dm ($PF_2$); −116.16 dm ($3CF_2$); $J^1_{P,F}$=890 Hz; $J^2_{P,F}$=92 Hz.

$^1H$ NMR (acetonitrile-$D_3$ film): 2.43 s ($CH_3$); 12.43 s ($H^+$).

Example 13

0.077 g of a 40% by weight aqueous hydrofluoric acid solution (1.54 mmol of HF) was mixed with 0.124 g of water (in total 9.44 mmol of water) in an FEP flask. While stirring using a magnetic stirrer, this mixture was cooled in an ice bath, and 0.836 g (1.15 mmol) of difluorotris(nonafluoro-n-butyl)phosphorane was added over the course of two minutes. All the phosphorane had dissolved within a further five minutes, and a colourless, clear solution of $[(C_4F_9)_3PF_3]^-H^+$ in water had formed. 1.037 g of this solution of trifluorotris(nonafluoro-n-butyl)phosphoric acid having a concentration of 83.6% by weight in water were obtained in virtually quantitative yield.

The solution was analysed by $^{19}F$ NMR spectroscopy. The spectra were measured using an FEP tube with an acetone-$D_6$ film as external lock and $CCl_3F$ as external reference.

$^{19}F$ NMR, δ, tpm: −44.91 dm (PF); −82.47 m ($3CF_3$); −87.29 dm ($PF_2$);

−112.32 m ($3CF_2$); −120.15 m ($1CF_2$); −122.52 m ($2CF_2$); −126.24 m ($3CF_2$); $J^1_{P,F}$=904 Hz; $J^1_{P,F}$=929 Hz.

Example 14

0.272 g (3.67 mmol) of dried diethyl ether in an FEP flask was cooled using an ice bath. While stirring using a magnetic stirrer, firstly 0.043 g (2.15 mmol) of hydrogen fluoride (HF) was slowly added to the diethyl ether and then 0.864 g (1.19 mmol) of difluorotris(nonafluoro-n-butyl)phosphorane was added over the course of five minutes. During the addition, all the phosphorane dissolved, and 1.17 g of a colourless, clear solution were prepared.

The solution was analysed by $^{19}F$ NMR spectroscopy. The spectra were measured using an FEP tube with an acetonitrile-$d_6$ film as external lock and $CCl_3F$ as internal reference.

The $^{19}F$ NMR spectrum confirmed that the acid $[(C_4F_9)_3PF_3]^-H^+$ (III) is formed.

$^{19}F$ NMR, δ, ppm: −44.17 dm (PF); −81.37 m ($3CF_3$); −84.76 dm ($PF_2$); −112.00 m ($3CF_2$); −119.18 m ($1CF_2$); −121.32 m ($2CF_2$); −125.15 m ($3CF_2$); $J^1_{P,F}$=907 Hz; $J^1_{P,F}$=939 Hz.

Example 15

0.68 g of an 18.3% by weight aqueous hydrofluoric acid solution (6.22 mmol of HF) was slowly added at 0° C. to 3.27 g (6.22 mmol) of trifluorobis(nonafluoro-n-butyl)-phosphorane while stirring using a magnetic stirrer. All the phosphorane had dissolved within three minutes, and a colourless, clear solution of $H^+[(n-C_4F_9)_2PF_4]^-$ in water formed. The yield was 3.95 g of a solution of tetrafluorobis(nonafluoro-n-butyl)phosphoric acid having a concentration of 85.9% by weight in water in virtually quantitative yield. The product conforms to the formula $H^+[(C_4F_9)_2PF_4]^-\cdot5H_2O$. The solution was analysed by $^{19}F$ NMR spectroscopy. The spectra were recorded using an FEP sample tube inside an NMR tube having a 5 mm thick wall, with an acetone-$D_6$ film being used as external lock and $CCl_3F$ in the film as reference.

$^{19}F$ NMR spectrum, δ, ppm: −70.72 dm ($PF_4$); −81.19t ($2CF_3$); −115.15 dm ($2CF_2$); −122.58 m ($2CF_2$); −124.77 t ($2CF_2$); $J^1_{P,F}$=958 Hz; $J^2_{P,F}$=105 Hz; $J^4_{F,F}$=9.3 Hz; $J^4_{F,F}$=16.4 Hz;

Example 16

0.713 g (1.67 mmol) of trifluorobis(heptafluoro-i-propyl) phosphorane was slowly added (over the course of 2 minutes) at 0° C. to 0.217 g of a 20.8% by weight, aqueous hydrofluoric acid solution (2.26 mmol of HF) while stirring using a magnetic stirrer. During this time, all the phosphorane dissolved, and a colourless, clear solution of tetrafluorobis(heptafluoro-i-propyl)phosphoric acid, $H^+[(i\text{-}C_3F_7)_2PF_4]^-$, in water formed.

The solution was analysed by $^{19}F$ NMR spectroscopy. The spectra were recorded using an FEP sample tube inside an NMR tube having a 5 mm thick wall, with an acetone-D6 film being used as external lock and $CCl_3F$ in the film as reference.

$^{19}F$ NMR spectrum, δ, ppm: −58.37 dm ($PF_4$); −71.23 m (4$CF_3$); −182.72 dm (2CF); $J^1_{P,F}$=955 Hz; $J^4_{P,F}$=78.4 Hz.

The signal of the excess HF was measured at 168.89 ppm in the $^{19}F$ NMR spectrum.

Example 17

6.57 g (36.7 mmol) of triethylene glycol dimethyl ether (triglyme) in an FEP flask were cooled by means of an ice bath. Firstly 0.74 g (37.0 mmol) of hydrogen fluoride (HF) was slowly added to the triglyme and then, over the course of five minutes, a further 14.90 g (35.0 mmol) of difluorotris (pentafluoroethyl)phosphorane were added while stirring the reaction mixture using the magnetic stirrer. After the reaction mixture had been stirred for a further hour at room temperature, 22.19 g of a yellow-brown, very viscous substance were obtained. Small amounts of this material were diluted with dichloromethane, and this solution was analysed by $^{19}F$ NMR spectroscopy. The spectra were recorded using an FEP sample tube inside a 5 mm NMR tube with an acetone-$D_6$ film as external lock and $CCl_3F$ as internal reference.

The $^{19}F$ NMR spectrum shows that in this case one mole of the acid $H^+[(C_2F_5)_3PF_3]^-$ are formed per mole of triglyme.

$^{19}F$ NMR spectrum of the meridionial form (approx. 90%): −44.41 dm (PF); −80.35 m ($CF_3$); −82.00 m (2$CF_3$); −87.94 dm ($PF_2$); −115.87 dm (3$CF_2$); $J^1_{P,F}$=890 Hz; $J^1_{P,F}$=891 Hz; $J^1_{P,F}$=90 Hz.

$^{19}F$ NMR spectrum of the facial form (approx. 10%): −68.29 dm; $J^1_{P,F}$=794 Hz ($PF_3$ group).

Some signals of the facial form overlap with those of the meridional form.

Example 18

6.78 g (16.9 mmol) of polyethylene glycol 400 (PEG 400) were introduced into an FEP flask and cooled using an ice bath. While stirring using the magnetic stirrer, firstly 0.79 g (39.5 mmol) of hydrogen fluoride (HF) was slowly added to the PEG 400 and then a further 15.27 g (35.8 mmol) of difluorotris(pentafluoroethyl)phosphorane were added over the course of three minutes. After this reaction mixture had been stirred at room temperature for 10 hours, 21.8 g of a yellow-brown, dense, gelatinous material were obtained. Small amounts of this material were diluted with dichloromethane, and the solution was analysed by $^{19}F$ NMR spectroscopy. The spectra were recorded using an FEP sample tube inside a 5 mm NMR tube with an acetone-$D_6$ film as external lock and $CCl_3F$ as internal reference.

The $^{19}F$ NMR spectrum shows that in this case the acid $H^+[(C_2F_5)_3PF_3]^-$ was formed in a polymeric matrix, approximately 2 mol of acid per mole of polyethylene glycol 400.

$^{19}F$ NMR spectrum of the meridional form (approx. 80%): −44.64 dm (PF); −80.48 m ($CF_3$); −82.07 m (2$CF_3$); −88.00 dm ($PF_2$); −115.94 dm (3$CF_2$); $J^1_{P,F}$=889 Hz; $J^1_{P,F}$=894 Hz; $J^2_{P,F}$=95 Hz.

$^{19}F$ NMR spectrum of the facial form (approx. 20%): −68.16 dm; $J^1_{P,F}$=788 Hz ($PF_3$ group).

Other signals of the facial form overlapped with those of the meridional form.

Example 19

The starting material, difluorotris(pentafluorophenyl) phosphorane, was prepared as follows: 0.711 g (1.34 mmol) of tris(pentafluorophenyl)phosphine in 5 $cm^3$ of dry toluene was mixed with 0.300 g (1.77 mmol) of xenon difluoride. The gas was liberated by heating the reaction mixture to from 50 to 60° C. The reaction was complete within 20 minutes. After the solvent had been evaporated under reduced pressure, 0.750 g of a white, solid substance was isolated. The yield of the difluorotris(pentafluoro-phenyl) phosphorane was 98.5 mol %. The $^{19}F$ NMR spectrum of the compound agrees with the spectra known from the literature (M. Fild and R. Schmutzler, J. Chem. Soc. (A), 1969, pp. 840–843).

0.50 g of dried diethyl ether and 0.107 g (0.187 mmol) of difluorotris(pentafluoro-phenyl)phosphorane in an FEP flask were cooled by means of an ice bath. Firstly 0.050 g (2.5 mmol) of hydrogen fluoride, HF, and then, over the course of two minutes, 0.3 g of triethylamine were added while the reaction mixture was stirred using the magnetic stirrer. During the addition, all the phosphorane dissolved, and triethylammonium hydrofluoride precipitated. After the sediment had been separated off and the solvent had been evaporated under reduced pressure 0.13 g of a viscous substance was isolated. Small amounts of this material were dissolved in acetone-$D_6$, and this solution was analysed by $^{19}F$ and $^1H$ NMR spectroscopy. The spectrum confirmed the formation of trifluorotris(pentafluorophenyl)phosphoric acid, $[(C_6F_5)_3PF_3]^-$ $H^+$, as a complex with triethylamine.

$^{19}F$ NMR spectrum (solvent: acetone-$D_6$; reference: $CCl_3F$, internal), δ, ppm: −6.73 dm (PF); −39.71 dm ($PF_2$); −132.06 m (4F); −134.75 m (2F); −160.42 t (1F); −161.24 t (2F); −166.20 m (6F); $J^1_{P,F}$=811 Hz; $J^1_{P,F}$=797 Hz; $J^3_{F,F}$=20 Hz.

$^1H$ NMR spectrum (solvent: acetone-$D_6$; reference: TMS, internal), δ, ppm: 1.27 t (3$CH_3$), 3.04 q (3$CH_2$), 12.11 s ($NH^+$); $J^3_{H,H}$=7.3 Hz.

Example 20

6.36 g (70.6 mmol) of dry dimethyl carbonate, $(CH_3O)_2CO$, in an FEP flask were cooled using an ice bath. Firstly 10.99 g (25.8 mmol) of difluorotris(pentafluoro-ethyl)phosphorane were slowly added to the dimethyl carbonate and then 0.615 g (30.7 mmol) of hydrogen fluoride (HF) was added to the reaction mixture over the course of 5 minutes while stirring using a magnetic stirrer. After the phosphorane had dissolved and the reaction mixture had been warmed to room temperature, 17.8 g of a colourless, clear solution were obtained.

The solution was analysed by $^{19}F$ NMR spectroscopy. The spectra were recorded using an FEP sample tube inside a 5 mm NMR tube with an acetone-$D_6$ film as external lock and $CCl_3F$ as internal reference.

The $^{19}F$ NMR spectrum shows that in this case the meridional structure of the acid $[(C_2F_5)_3PF_3]^-H^+$ is formed.

$^{19}$F NMR spectrum: −44.34 dm (PF); −80.26 m (CF$_3$); −81.93 m (2CF$_3$); −87.78 dm (PF$_2$); −115.85 dm (3CF$_2$); J$^1_{P,F}$=889 Hz; J$^1_{P,F}$=92 Hz.

$^1$H NMR spectrum (acetone-D$_3$ film, standard: TMS): 4.49 s (CH$_3$); 17.54 s (H$^+$).

Applications of Trifluorotris(perfluoroalkyl)phosphoric Acids

Example 21

12.15 g of an 83.2% by weight, aqueous trifluorotris(pentafluoroethyl)phosphoric acid (prepared as described in Example 1) were neutralised at 0° C. with stirring by addition of 0.95 g lithium hydroxide monohydrate in small portions. 13.1 g of a clear solution of lithium trifluorotris(pentafluoroethyl) phosphate having a concentration of 78.2% by weight in water were obtained. The yield of the lithium trifluorotris(pentafluoroethyl)phosphate was virtually quantitative. The solution was analysed by $^{19}$F NMR spectroscopy. The spectra were recorded using an FEP sample tube inside a 5 mm NMR tube with an acetone-D$_6$ film as external lock and CCl$_3$F in the film as reference.

$^{19}$F NMR spectrum, δ, ppm: −43.48 dm (PF); −79.54 m (CF$_3$); −81.30 m (2CF$_3$); −88.07 dm (PF$_2$); −114.21 dm (3CF$_2$); J$^1_{P,F}$=891 Hz; J$^1_{P,F}$=908 Hz; J$^2_{P,F}$=92 Hz.

Example 22

20.44 g of an 83.2% by weight, aqueous trifluorotris(pentafluoroethyl)phosphoric acid (prepared as described in Example 1) were neutralised by addition of 1.42 g of lithium carbonate in small portions with stirring. The yield was 21.0 g of a clear solution of lithium trifluorotris(pentafluoroethyl)phosphate in a concentration of 82.0% by weight in water. The yield of the lithium trifluotris(pentafluroethyl) phosphate was virtually quantitative. The solution was analysed by $^{19}$F NMR spectroscopy. The spectra were recorded using an FEP sample tube inside a 5 mm NMR tube with an acetone-D$_6$ film as external lock and CCl$_3$F in the film as reference.

$^{19}$F NMR spectrum, δ, ppm: −43.31 dm (PF); −79.44 m (CF$_3$); −81.19 m (2CF$_3$); −87.96 dm (PF$_2$); −114.20 dm (3CF$_2$); J$^1_{P,F}$=891 Hz; J$^1_{P,F}$=907 Hz; J$^2_{P,F}$=92 Hz.

Example 23

A solution of 6.38 g (14.3 mmol) of trifluorotris(pentafluoroethyl)phosphoric acid in 1.9 g of diethyl ether (prepared analogously to the process in Example 7) was neutralised by slow addition of 6.0 cm$^3$ (15.0 mmol) of a 2.5 M solution of butyllithium in hexane at 0° C. with stirring. The mixture was stirred for a further half an hour, and the complex of lithium trifluorotris(pentafluoroethyl)phosphate with diethyl ether (bottom, pale-yellow, viscous layer) was separated off from the hexane (upper layer).

The $^{19}$F NMR spectrum of the diethyl ether solution showed the presence of lithium trifluorotris(pentafluoroethyl)phosphate, which was obtained in virtually quantitative yield. The spectra were recorded using an FEP sample tube inside a 5 mm NMR tube with an acetone-D$_6$ film as external lock and CCl$_3$F in the film as reference.

$^{19}$F NMR spectrum of the meridional form (approx. 85 mol %): −47.19 dm (PF); −79.80 m (CF$_3$); −81.34 m (2CF$_3$); −88.77 dm (PF$_2$); −114.84 dm (3CF$_2$); J$^1_{P,F}$=867 Hz; J$^1_{P,F}$=905 Hz; J$^2_{P,F}$=92 Hz.

$^{19}$F NMR spectrum of the facial form (approx. 15 mol %): −66.88 dm; J$^1_{P,F}$=776 Hz (PF$_3$ group).

Other signals of the facial form overlapped with those of the meridional form.

Example 24

10.77 g of an 83.2% by weight, aqueous trifluorotris(pentafluoroethyl)phosphoric acid (prepared as described in Example 1) were diluted with 10 cm$^3$ of water and neutralised with 1.52 g of magnesium hydroxycarbonate (Merck, proportion of the Mg cation at least 24%) in small portions with cooling in an ice bath and with stirring. The excess magnesium hydroxycarbonate was filtered off, and the solution of the magnesium trifluorotris(pentafluoroethyl)phosphate in water was analysed by $^{19}$F NMR spectroscopy. The spectra were recorded using an FEP sample tube inside a 5 mm NMR tube with an acetone-D$_6$ film as external lock and CCl$_3$F in the film as reference.

$^{19}$F NMR spectrum, δ, ppm: −43.34 dm (PF); −79.35 m (CF$_3$); −80.99 m (2CF$_3$); −88.11 dm (PF$_2$); −114.54 dm (3CF$_2$); J$^1_{P,F}$=874 Hz; J$^1_{P,F}$=899 Hz; J$^2_{P,F}$=91 Hz.

Example 25

7.19 g of an 83.2% by weight, aqueous trifluorotris(pentafluoroethyl)phosphoric acid (prepared as described in Example 1) were diluted with 10 cm$^3$ of water with cooling in an ice bath and with stirring and neutralised by addition of 1.76 g of zinc hydroxycarbonate (Fluka, proportion of Zn cation≧58%) in small portions. The excess zinc hydroxycarbonate was filtered off, and the solution of zinc trifluorotris(pentafluoro-ethyl) phosphate in water was analysed by $^{19}$F NMR spectroscopy. The spectra were recorded using an FEP sample tube inside a 5 mm NMR tube with an acetone-D$_6$ film as external lock and CCl$_3$F in the film as reference.

$^{19}$F NMR spectrum, δ, ppm: −43.40 dm (PF); −79.56 m (CF$_3$); −81.23 m (2CF$_3$); −87.91 dm (PF$_2$); −114.45 dm (3CF$_2$); J$^1_{P,F}$=890 Hz; J$^1_{P,F}$=913 Hz; J$^2_{P,F}$=96 Hz.

Example 26

10.78 g of an 83.2% by weight, aqueous trifluorotris(pentafluoroethyl)phosphoric acid (prepared as described in Example 1) were diluted with 10 cm$^3$ of water in an ice bath with stirring and neutralised with 2.78 g of copper(II) hydroxycarbonate in small portions. The excess copper hydroxycarbonate was filtered off, and the solution of copper trifluorotris(pentafluoroethyl)phosphate in water was analysed by $^{19}$F NMR spectroscopy. The spectra were recorded using an FEP sample tube inside a 5 mm NMR tube with an acetone-D$_6$ film as external lock and CCl$_3$F in the film as reference.

$^{19}$F NMR spectrum of the meridional form, δ, ppm: −47.88 dm (PF); −84.03 m (CF$_3$); −85.59 m (2CF$_3$); −92.70 dm (PF$_2$); −119.27 dm (3CF$_2$); J$^1_{P,F}$=895 Hz; J$^2_{P,F}$=87 Hz.

The small signal of the facial form of the copper salt was also present in the spectrum: −71.44 d (PF$_3$); J$^1_{P,F}$=790 Hz.

Example 27

3.10 g of a 73.0% by weight, aqueous trifluorotris(pentafluoroethyl)phosphoric acid (prepared as described in Example 3) were diluted with 5 cm$^3$ of water with cooling in a water bath and with stirring and neutralised with 0.74 g of silver carbonate in small portions. The excess silver carbonate was filtered off, and the solution of silver trifluorotris(pentafluoroethyl) phosphate in water was analysed by $^{19}$F NMR spectroscopy. The spectra were recorded using an FEP sample tube inside a 5 mm NMR tube with an acetone-$D_6$ film as external lock and $CCl_3F$ in the film as reference.

$^{19}$F NMR spectrum, δ, ppm: −42.60 dm (PF); −78.66 m ($CF_3$); −80.35 m (2$CF_3$); −87.41 dm (P$F_2$); −114.06 dm (3$CF_2$); $J^1_{P,F}$=890 Hz; $J^2_{P,F}$=92 Hz.

Example 28

A solution of 16.68 g (37.4 mmol) of trifluorotris(pentafluoroethyl)phosphoric acid in 14.52 g of diethyl ether (prepared as described in Example 7) was slowly added at room temperature with stirring to 20.50 g of a 50% by weight solution of tetra-(n-butyl)phosphonium chloride (10.25 g or 34.8 mmol) in toluene. The mixture was stirred for a further 30 minutes, and the solvent mixture was distilled off at a reduced pressure of 13.3 Pa. 24.46 g of a white, solid substance were obtained in this way. The yield of tetra(n-butyl)phosphonium trifluorotris(pentafluoroethyl) phosphate was virtually quantitative. The melting point after crystallisation from a methanol/water mixture was 73–74° C.

Analysis: C 37.31%, H 5.06%; calculated: 37.51%, H 5.15%.

$^{19}$F NMR spectrum (solvent: acetone-$D_6$; reference: $CCl_3F$ internal): −43.83 dm (PF); −79.72 m (C$F_3$); −81.23 m (2C$F_3$); −86.77 dm (P$F_2$); −115.43 dm (3C$F_2$); $J^1_{P,F}$=890 Hz; $J^1_{P,F}$=905 Hz; $J^2_{P,F}$=92 Hz.

$^1$H NMR spectrum (solvent, acetone-$D_6$; reference: TMS internal): 0.95 t (4C$H_3$), 1.57 m (8C$H_2$), 2.34 m (4C$H_2$).

Example 29

11.37 g of a 20% by weight, aqueous solution of tetraethylammonium hydroxide were slowly added (over the course of 2 minutes) with stirring and cooling in an ice bath to 8.28 g of an 83.2% by weight aqueous trifluorotris (pentafluoroethyl)phosphoric acid (prepared as described in Example 1). The reaction mixture was diluted with 100 cm$^3$ of water and stirred at room temperature for a further 10 minutes. A white sediment was filtered off and washed twice with 30 cm$^3$ of water. After drying overnight in air, 8.55 of a white, solid material were obtained. The yield of tetraethylammonium trifluorotris(pentafluoroethyl)phosphate was 96.3%. Analysis: C 29.14%, H 3.40%, N 2.49%; calculated: C 29.23%, H 3.50%, N 2.43%. The melting point after crystallisation of this product from a methanol/water mixture was unchanged at 95° C.

$^{19}$F NMR spectrum (solvent: acetone-$D_6$; reference: $CCl_3F$ internal): −43.78 dm (PF); −79.69 m (C$F_3$); −81.24 m (2C$F_3$); −86.80 dm (P$F_2$); −115.36 dm (3C$F_2$); $J^1_{P,F}$=889 Hz; $J^1_{P,F}$=906 Hz; $J^2_{P,F}$=89 Hz.

$^1$H NMR spectrum (solvent: acetone-$D_6$; reference: TMS internal): 1.39 tm (4C$H_3$), 3.48 q (4C$H_2$); $J^3_{H,H}$=7.3 Hz.

Example 30

10.85 g of a 73.0% by weight, aqueous trifluorotris (pentafluoroethyl)phosphoric acid (prepared as described in Example 3) were added slowly over the course of 3 minutes with stirring and cooling in an ice-water bath to 81.47 g of aqueous tetramethyl-ammonium hydroxide (prepared from 6.47 g of a 25% by weight aqueous $(CH_3)_4N^+$$^-$OH by dilution with 75 cm$^3$ of water). The reaction mixture was stirred at room temperature for a further 10 minutes. A white sediment was filtered off and washed three times with 30 cm$^3$ of water. After drying overnight in air, 8.55 g of a white, solid material were obtained. The yield of tetramethylammonium trifluorotris-(pentafluoroethyl)phosphate was 95.2%. The melting point was 112° C.

$^{19}$F NMR spectrum (solvent: acetone-$D_6$; reference: $CCl_3F$ internal): −43.70 dm (PF); −79.70 m (C$F_3$); −81.24 m (2C$F_3$); −86.75 dm (P$F_2$); −115.43 dm (3C$F_2$); $J^1_{P,F}$=889 Hz; $J^2_{P,F}$=88 Hz.

$^1$H NMR spectrum (solvent: acetone-$D_6$; reference: TMS internal): 3.42 s (4C$H_3$).

Example 31

3.95 g of an 85.9% by weight aqueous tetrafluorobis (nonafluoro-n-butyl)phosphoric acid (prepared as described in Example 15) were slowly added over the course of 3 minutes to 54.58 g of aqueous tetraethylammonium hydroxide (prepared from 4.58 g of a 20% by weight, aqueous $(C_2H_5)_4N^+$$^-$OH solution by dilution with 50 cm$^3$ of water) with stirring and with cooling of the reaction mixture in an ice bath. The reaction mixture was stirred at room temperature for a further 10 minutes. A white sediment was filtered off and washed twice with 10 cm$^3$ of water. After drying overnight in air, 3.05 g of a white, solid material were obtained. The yield of tetraethylammonium tetrafluorobis (nonafluoro-n-butyl)phosphate was 72.6%.

$^{19}$F NMR spectrum (solvent: acetone-$D_6$; reference: $CCl_3F$ internal): −70.20 dm (P$F_4$); −80.87 m (2C$F_3$); −116.04 dm (2C$F_2$); −122.34 m (2C$F_2$); −124.61 t (2C$F_2$); $J^1_{P,F}$=930 Hz; $J^2_{P,F}$=94 Hz; $J^4_{P,F}$=15.7 Hz.

$^1$H NMR spectrum (solvent: acetone-$D_6$; reference: TMS internal): 1.38 tm (4C$H_3$), 3.48 q (4C$H_2$); $J^3_{H,H}$=7.3 Hz.

Example 32

0.030 g of lithium powder was added in small portions at room temperature and with stirring using a magnetic stirrer to 1.72 g of a solution of trifluorotris(pentafluoroethyl) phosphoric acid in dimethyl carbonate, prepared as described in Example 20. At the beginning, the reaction mixture reacted vigorously with evolution of hydrogen. Complete reaction of the reaction components was achieved by warming the reaction mixture to 60° C. over a period of 30 minutes.

After the excess lithium powder had been separated off, the solution of lithium trifluorotris(pentafluoroethyl)phosphate in dimethyl carbonate was analysed by $^{19}$F NMR and $^1$H NMR spectroscopy. The spectra were recorded using an FEP sample tube inside a 5 mm NMR tube with an acetone-$D_6$ film as external lock and $CCl_3F$ in the film as reference.

$^{19}$F NMR spectrum of the meridional form (≈85 mol %): −44.53 dm (PF); −79.90 m (C$F_3$); −81.71 m (2C$F_3$); −87.77 dm (P$F_2$); −115.23 dm (3C$F_2$); $J^1_{P,F}$=888 Hz; $J^2_{P,F}$=91 Hz.

$^{19}$F NMR spectrum of the facial form (≈15 mol %): −67.98 dm; $J^1_{P,F}$=785 Hz (P$F_3$ group). Other signals of the facial form overlapped with those of the meridional form.

$^1$H NMR spectrum (acetone-$D_3$ film, reference: TMS): 4.35 s (C$H_3$).

Example 33

16.09 g of trifluorotris(pentafluoroethyl)phosphoric acid in dimethyl carbonate, prepared as described in Example 20, were diluted with 6.78 g of dry dimethyl carbonate and reacted with 0.25 g of lithium hydride, which was added to the reaction mixture in small portions with stirring using a magnetic stirrer and with cooling in an ice bath. At the beginning, this reaction mixture reacted vigorously with evolution of hydrogen. When all the lithium hydride had been added, the mixture was warmed to room temperature and stirred for a further hour.

After the excess lithium hydride had been separated off, the solution of lithium trifluorotris(pentafluoroethyl)phosphate in dimethyl carbonate was analysed by $^{19}$F NMR and $^1$H NMR spectroscopy. The spectra were recorded using an FEP sample tube inside a 5 mm NMR tube with an acetone-D$_6$ film as external lock and CCl$_3$F as internal reference.

$^{19}$F NMR spectrum of the meridional form ($\approx$85 mol %): −44.07 dm (PF); −80.12 m (CF$_3$); −81.77 m (2CF$_3$), −87.52 dm (PF$_2$); −115.17 dm (3CF$_2$): $J^1_{P,F}$=888 Hz; $J^2_{P,F}$=87 Hz.

$^{19}$F NMR spectrum of the facial form ($\approx$15 mol %): −68.40 dm; $J^1_{P,F}$=795 Hz (PF$_3$ group). Other signals of the facial form overlapped with those of the meridional form.

$^1$H NMR spectrum (acetone-D$_3$ film, standard: TMS): 4.21 s (CH$_3$).

This solution can be employed directly for the preparation of electrolytes for lithium batteries.

The invention claimed is:

1. An acid of the formula [I]

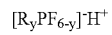
[R$_y$PF$_{6-y}$]$^-$H$^+$ [I]

where
y=1, 2 or 3,
and wherein
the ligands R may be identical or different, and
R is a perfluorinated C$_{1-8}$-alkyl or aryl group or R is a partially fluorinated C$_{1-8}$-alkyl or aryl group wherein optionally some of the F or H are substituted by chlorine.

2. An acid according to claim 1, wherein at least one R is a nonafluorobutyl or pentafluorophenyl group.

3. An acid according to claim 1, wherein y =2 or 3.

4. An acid according to claim 1, wherein the acid is: trifluorotris(pentafluoroethyl)phosphoric acid, trifluorotris(heptafluoro-n-propyl)phosphoric acid, trifluorotris(nonafluoro-n-butyl)phosphoric acid, tetrafluorobis(nonafluoro-n-butyl)phosphoric acid, pentafluoro(nonafluoro-n-butyl)phosphoric acid, or tetrafluorobis(heptafluoro-i-propyl)phosphoric acid.

5. A process for the preparation of an acid according to claim 1, which comprises reacting a perfluoroalkylphosphorane with hydrogen fluoride in the presence of a suitable solvent and/or proton acceptor.

6. A process according to claim 5, wherein the solvent and/or proton acceptor employed is water, an alcohol, an ether, a sulfide, an amine, a phosphine, a carboxylic acid, an ester, a glycol, a polyglycol, a polyamine, a polysulfide or a mixture of at least two of these solvents and/or proton acceptors.

7. A process according to claim 6, wherein the suitable solvent and/or proton acceptor is methanol, ethanol, acetic acid, dimethyl ether, diethyl ether, dimethyl carbonate, dimethyl sulfide, dimethylformamide, triethylamine, triphenylphosphine, or a mixture of at least two of these compounds.

8. A process according to claim 5, the reaction of the perfluoroalkylphosphorane with hydrogen fluoride is carried out in a solution having a concentration of greater than 0.1% by weight of HF, but less than 100% by weight, of HF.

9. A process according to claim 5, wherein the reaction of the perfluoroalkylphosphorane is carried out at a temperature of from −50 to +100° C.

10. A solution of an acid according to claim 1, and a solvent, wherein the acid is present in a concentration of greater than 2% by weight.

11. A salt of the formula [II]

[R$_y$PF$_{6-y}$]$_m$·M$^{m+}$ [II]

where
M$^{m+}$ is a Zn, Mg, Cu, ammonium, phosphonium, oxonioum, sulfonium, tropilium, nitryl, nitrosyl, tris(dialkylammino)carbonium, calcium, strontium, barium, scandium, yttrium, ytterbium, lanthanum, aluminum, indium, or cadmium cation,
m =1, 2 or 3,
and y =1, 2 or 3,
and wherein
the ligands R may be identical or different, and
R is a perfluorinated C$_{1-8}$-alkyl or aryl group or R is a partially fluorinated C$_{1-8}$-alkyl or aryl group wherein optionally some of the F or H are substituted by chlorine.

12. A salt of the formula [II] according to claim 11, wherein the salt comprises a Zn, Mg, Cu, ammonium, phosphonium, oxonioum, sulfonium, arsonium, tropilium, nitryl, nitrosyl, or a tris(dialkylammino)carbonium cation.

13. A process for the preparation of a salt according to claim 11, which comprises reacting an acid of the formula [R$_y$PF$_{6-y}$]$^-$H$^+$, wherein R and y are defined in claim 11, in a suitable solvent with a salt of the formula [III]

M$^{m+}$(A)$^{m-}$ [III]

where
M$^{m+}$ is as defined in claim 11,
A is a basic or neutral anion or a mixture of basic anions or a mixture of at least one basic and at least one neutral anion,
and m=1, 2 or 3,
or with a metal, a metal hydride, a metal oxide, or a metal hydroxide wherein the metal is the one that will provide the M$^{m+}$ cation.

14. A process according to claim 13, wherein the salt of the formula [III] comprises at least one oxide, hydride, carbonate, hydroxide, chloride, fluoride, formate, acetate and/or trifluoroacetate anion.

15. A process according to claim 13, wherein the acid is reacted with at least one metal which is Rb, Mg, Cs, Ca, Sr, Ba, Sc, Y, Yb, La, Al, In, Cd and/or Zn.

16. A process according to claim 13, wherein the acid is reacted with at least one oxide which is, MgO, CaO, SrO, BaO, Sc$_2$O$_3$, Y$_2$O$_3$, Yb$_2$O$_3$, La$_2$O$_3$, Al$_2$O$_3$, CdO, ZnO, CuO, FeO and/or Fe$_2$O$_3$.

17. A process according to claim 13, wherein the acid is reacted with at least one hydroxide which is, RbOH, CsOH, Mg(OH)$_2$, Ca(OH)$_2$, Sr(OH)$_2$, Ba(OH)$_2$, Cd(OH)$_2$, Zn(OH)$_2$, Sc(OH)$_3$, Al(OH)$_3$ and/or Cu(OH)$_2$.

18. A process according to claim 13, wherein the acid is reacted with at least one hydride which is, CaH$_2$, YH$_3$ and/or AlH$_3$.

19. A method for preparing an organic compound, using a catalyst, wherein the catalyst comprises an acid according to claim 1.

20. A method for replacing an acid $HPF_6$ and/or $HBF_4$ in a chemical reaction, comprising providing a replacement acid, which comprises an acid according to claim 1.

21. An acid according to claim 1, wherein at least one R is a pentafluoroethyl group.

* * * * *